United States Patent
Riordan et al.

(10) Patent No.: US 9,205,112 B2
(45) Date of Patent: Dec. 8, 2015

(54) COMBINATION TREATMENT OF CARDIOVASCULAR DISEASE

(75) Inventors: Neil Riordan, Tempe, AZ (US); Fabio Salazar, San Jose (CR); Thomas E. Ichim, San Diego, CA (US)

(73) Assignee: Creative Medical Health, Inc., Phoenix, AZ (US)

( * ) Notice: Subject to any disclaimer, the term of this patent is extended or adjusted under 35 U.S.C. 154(b) by 1469 days.

(21) Appl. No.: 12/108,130

(22) Filed: Apr. 23, 2008

(65) Prior Publication Data

US 2008/0260704 A1    Oct. 23, 2008

Related U.S. Application Data

(60) Provisional application No. 60/913,531, filed on Apr. 23, 2007.

(51) Int. Cl.

| | |
|---|---|
| *A01N 63/00* | (2006.01) |
| *A61K 31/00* | (2006.01) |
| *A61K 31/34* | (2006.01) |
| *C12N 5/00* | (2006.01) |
| *C12N 5/06* | (2006.01) |
| *C12N 5/08* | (2006.01) |
| *A61K 35/34* | (2015.01) |
| *A61K 35/28* | (2015.01) |
| *A61K 35/44* | (2015.01) |
| *A61K 38/44* | (2006.01) |
| *A61K 45/06* | (2006.01) |
| *A61K 31/05* | (2006.01) |
| *A61K 31/203* | (2006.01) |
| *A61K 31/366* | (2006.01) |
| *A61K 31/375* | (2006.01) |
| *A61K 31/385* | (2006.01) |
| *A61K 31/519* | (2006.01) |
| *A61K 31/7048* | (2006.01) |
| *C12N 5/07* | (2010.01) |
| *C12N 5/078* | (2010.01) |

(52) U.S. Cl.
CPC .............. *A61K 35/34* (2013.01); *A61K 31/05* (2013.01); *A61K 31/203* (2013.01); *A61K 31/366* (2013.01); *A61K 31/375* (2013.01); *A61K 31/385* (2013.01); *A61K 31/519* (2013.01); *A61K 31/7048* (2013.01); *A61K 35/28* (2013.01); *A61K 35/44* (2013.01); *A61K 38/446* (2013.01); *A61K 45/06* (2013.01); *A61K 2300/00* (2013.01); *C12N 5/06* (2013.01); *C12N 5/0634* (2013.01)

(58) Field of Classification Search
CPC ........ C12N 5/06; C12N 5/0634; A61K 35/28; A61K 31/375; A61K 2300/00
USPC .............. 424/93.7; 435/325, 355, 372; 514/1, 514/474
See application file for complete search history.

(56) References Cited

U.S. PATENT DOCUMENTS 6,448,287 B1 *    9/2002   Casciari et al. ................ 514/440

OTHER PUBLICATIONS

Wu et al., 2012, Ageing Research Reviews, vol. 11, p. 32-40.*
Stamm et al., 2006, Cell Transplantation, vol. 15, Supplement 1, pp. 47-56, Abstract.*
March et al., 2004, Am J Physiol Heart Circ Physiol, vol. 287, p. H458-H463.*
Emmerich, Joseph, 2009, Bulletin de l'Academie Nationale de Medicine, vol. 193, No. 3, Abstract.*
Capoccia et al., 2009, Blood, vol. 113, No. 21, p. 5340-5351.*
Allegrucci et al., 2006, Human Reproduction Update, Vol. Advance Access published on Aug. 26, 2006, p. 1-18.*
Sato et al., 2003, Developmental Biology, vol. 260, p. 404-413.*
Rao, M., 2004, Developmental Biology, vol. 275, p. 269-286.*
Abeyta et al., 2004, Human Molecular Genetics, vol. 13, No. 6, p. 601-608.*
Kihm, Anthony J., 2007, US 20070160588 A1.*
Litvack, F., 2005, US 20050271697 A1.*
Iwase et al., 2005, Cardiovascular Research, vol. 66, p. 543-551.*
Blum et al., 2012, Atheroclerosis, vol. 223, p. 269-277.*
Smith, Milton, 2004, US 20040071770 A1.*
Durdu et al., 2006, J Vasc Surg, vol. 44, p. 732-739.*
Higashi, Yukihito, 2006, Current Pharmaceutical Biotechnology, vol. 7, No. 2, Abstract.*

* cited by examiner

*Primary Examiner* — Shin Lin Chen
(74) *Attorney, Agent, or Firm* — Baumgartner Patent Law; Marc Baumgartner

(57) ABSTRACT

Disclosed are methods, compositions of matter and cells for treatment of cardiovascular disease through concurrent inhibition of oxidative stress while administration of a cell therapy. The invention also concerts the modulation of oxidative stress for preferential induction of differentiation while concurrently inhibiting inflammatory processes that decrease efficacy of cellular therapy.

8 Claims, No Drawings

COMBINATION TREATMENT OF CARDIOVASCULAR DISEASE

CROSS-REFERENCE TO RELATED APPLICATIONS

This application claims priority to Provisional Application Ser. No. 60/913,531, filed Apr. 23, 2007 and entitled "Combination Treatment of Cardiovascular Disease", which is hereby expressly incorporated by reference in its entirety.

FIELD OF THE INVENTION

The invention relates to treatment of cardiovascular disease. Particularly, the invention relates to methods of treatment comprising of, inter alia, combination treatment of cells and antioxidants. More particularly, the invention relates to utilization of antioxidants to enhance efficacy of cells with ability to ameliorate or significantly reduce cardiovascular disease.

BACKGROUND

Acute myocardial infarction (heart attack) is a major cause of morbidity and mortality with a reported annual incidence of 1.1 million cases in the United States alone. It is despite the increasing use of cholesterol lowering agents and attentiveness to co-morbid illnesses. Subsequent to infarction, a variety of inflammatory and other changes are known to occur which despite proper reperfusion by thrombolytics and/or stenting, contribute to cardiac remodeling and eventual heart failure. Numerous other cardiac conditions are widely prevalent, particularly myocardial ischemia which is associated with atherosclerosis of arteries feeding myocardial tissue. Congenital and acquired cardiac abnormalities are numerous and range from valvular defects to hypertrophy to septal defects.

Cellular therapy of cardiovascular diseases has achieved some degree of success. For example, administration of autologous bone marrow stem cells has been demonstrated to benefit patients with end-stage chronic ischemic cardiomyopathy (1, 2). Additionally, administration of similar stem cell populations subsequent to the stunning phase of acute myocardial infarction has been demonstrated to induce an increase in left ventricular ejection fraction as compared to control patients (3). The methods by which stem cells induce therapeutic effect in cardiovascular diseases include induction of angiogenesis (4), inhibition of ventricular remodeling (5), and transdifferentiation into cardiomyocytes (6). Additionally, besides stem cells, skeletal muscle cells have also been used for treatment of cardiovascular diseases (7).

Numerous patents have been issued on utilizing stem cells for treatment of cardiovascular disease. For example, U.S. Pat. No. 7,166,280 entitled "Combination growth factor therapy and cell therapy for treatment of acute and chronic heart disease" teaches the combination of growth factor administration together with stem cell administration. Some of the growth factors mentioned in the patent have already been used for treatment of heart disease such as FGF and VEGF members. Additionally, it is important to note that others have already demonstrated synergy between administration of these types of growth factors together with stem cells. U.S. Pat. No. 6,387,369 entitled "Cardiac muscle regeneration using mesenchymal stem cells" discloses the use of mesenchymal stem cells for cardiac repair, specifically after myocardial infarction.

To date, no combination therapy has been reported that concurrently inhibits oxidative stress and administers stem cells. Although reports exist of utilizing nutritional intervention together with stem cell therapy (8), these do not induce substantive antioxidant effect. Given that stem cells are known to be sensitive to oxidative stress, the current invention provides, inter alia, a method of increasing efficacy of stem cell therapy through concurrent administration of antioxidants with said stem cell therapy.

SUMMARY

Embodiments herein relate to methods of treating cardiovascular disease comprising: a) identifying a subject suffering from cardiovascular disease; b) administering one or more cell populations capable of ameliorating cardiovascular disease to said subject in a sufficient amount such that said cardiovascular disease is ameliorated; and c) administering an antioxidant to subject in sufficient amount to enhance the amelioration of cardiovascular disease by said one or more cell populations.

The term cardiovascular disease, as used herein can non-exclusively be selected from a group consisting of: cardiomyopathy, post myocardial infarction scarring, myocardial ischemia, coronary artery disease, peripheral vascular disease, CNS vascular disease, congestive heart failure, ventricular septal defect, a valvular defect, atrial septal defect, a congenital heart defect, ventricular aneurysm, a condition requiring ventricular reconstruction, restenosis, cardiac hypertrophy, and heart failure.

Preferably, the one or more cell populations capable of ameliorating cardiovascular disease are selected from the group consisting of: differentiated cells, progenitor cells, and stem cells. Advantageously, differentiated cells can be selected from the group consisting of: myocytes, cardiomyocytes, and striated muscle cells. In further embodiments, progenitor cells can be selected from the group consisting of: endothelial progenitor cells, cardiovascular progenitor cells, and hematopoietic progenitor cells. In other embodiments, stem cells can be selected from the group consisting of: embryonic stem cells, cord blood stem cells, placental stem cells, bone marrow stem cells, amniotic fluid stem cells, amniotic membrane stem cells, menstrual blood derived stem cells, endometrial regenerative cells, neuronal stem cells, circulating peripheral blood stem cells, mesenchymal stem cells, germinal stem cells, adipose tissue derived stem cells, exfoliated teeth derived stem cells, hair follicle stem cells, dermal stem cells, parthenogenically derived stem cells, reprogrammed stem cells and side population stem cells.

The one or more cell populations provided herein can include both mesenchymal stem cells and CD34 cells.

Preferred antioxidants used herein can be selected from the group consisting of: ascorbic acid and derivatives thereof, alpha tocopherol and derivatives thereof, rutin, quercetin, ascorbic acid, allopurinol, hesperedin, lycopene, resveratrol, tetrahydrocurcumin, rosmarinic acid, Ellagic acid, chlorogenic acid, oleuropein, alpha-lipoic acid, glutathione, polyphenols, pycnogenol, retinoic acid, ACE Inhibitory Dipeptide Met-Tyr, recombinant superoxide dismutase, xenogenic superoxide dismutase, and superoxide dismutase, for example.

In preferred embodiments, the antioxidant can be administered to the subject prior to, concurrently with, or subsequent to the administration of said one or more cell populations and at a concentration sufficient to reduce oxidative stress from inhibiting the ameliorating effects of said one or more cell populations on said cardiovascular disease.

Further methods can include measuring the oxidative stress in the subject prior to the administration of said one or more cell populations, and wherein the antioxidant is administered at a concentration and frequency based upon said measurement of oxidative stress.

An additional method of treating cardiovascular disease can include: a) identifying a subject suffering from cardiovascular disease; b) administering a mesenchymal stem cell population to said subject; b) administering a CD34 positive stem cell population to said subject; and c) administering ascorbic acid intravenously to said subject in a combined amount sufficient to ameliorate said cardiovascular disease.

The mesenchymal stem cell population preferably expresses one or more markers selected from the group consisting of: STRO-1, CD105, CD54, CD106, HLA-I markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD10, CD13, STRO-2, VCAM-1, CD146, and THY-1. According to more specific embodiments, the mesenchymal stem cell population does not express substantial levels of the markers selected from the group consisting of: HLA-DR, CD117, and CD45.

The mesenchymal stem cell population can be derived from sources selected from the group consisting of: bone marrow, adipose tissue, umbilical cord blood, placental tissue, peripheral blood mononuclear cells, differentiated embryonic stem cells, and differentiated progenitor cells, for example.

According to other embodiments, the CD34 positive stem cell population possesses angiogenic activity. Additionally, the CD34 positive stem cell population can possess hematopoietic activity. CD34 positive stem cell population can be derived from multiple sources, non-exclusively including: mobilized peripheral blood, peripheral blood, cord blood, bone marrow, and embryonic stem cells. The CD34 positive stem cell population can be expanded in vitro prior to administration to subject, according to advantageous methods.

Preferably, the ascorbic acid is administered to the subject at a frequency and concentration sufficient to enhance the ameliorating effects of said mesenchymal stem cell population and said CD34 positive stem cell population. For example, the ascorbic acid can be administered to said subject intravenously at 15-700 grams per week. According to preferred embodiments, the ascorbic acid is administered together with lipoic acid and/or a water soluble salt of lipoic acid. A preferred administration of ascorbic acid is 100-1000 milligrams per day together with lipoic acid and/or a water soluble salt of lipoic acid. Alternatively, the ascorbic acid can be administered to said subject at 300-600 milligrams per day together with lipoic acid and/or a water soluble salt of lipoic acid. In advantageous embodiments, the ascorbic acid is administered to the subject together with lipoic acid and/or a water soluble salt of lipoic acid at a respective ratio of 1:1 to 3500:1. In still further embodiments, the ascorbic acid is administered to the subject together with lipoic acid and/or a water soluble salt of lipoic acid at a respective ratio of 10:1 to 100:1. The methods herein can further include administering one or more growth factors to said subject.

DETAILED DESCRIPTION

The invention teaches methods of treating cardiovascular disease through administration of cells with cardio-reparative potential in an environment that has been modified through administration of one or more antioxidants. It is known that numerous cardiovascular conditions are associated with increased levels of oxidative stress and inflammatory changes. For example, circulating levels of C-reactive protein (CRP), a marker of inflammation are associated with extent of atherosclerosis (9). Elevated levels of CRP are also predictive of coronary heart disease and found increased in valvular heart disease (10, 11). It is believed that causes of inflammation are associated with increased oxidative stress, and in some cases said oxidative stress is actually causative of inflammation. For example, an inverse correlation has been demonstrated between plasma ascorbic acid and CRP levels in patients with peripheral artery disease (12). Administration of ascorbic acid and various other antioxidants has been demonstrated to decrease CRP levels in patients with a variety of inflammatory associated conditions (13, 14).

Administration of cellular therapy for treatment of cardiovascular disease is based on the notion of inducing angiogenesis, and/or inducing differentiation into functional tissue, and/or providing trophic support for endogenous cells to replace damaged tissue. The introduction of cells to a patient with cardiovascular disease implies cells are implanted in an environment associated with inflammation. For example, subsequent to myocardial infarction, oxidative stress from the direct ischemia reperfusion injury, as well as subsequent cellular infiltration, is associated with increased scar tissue formation and subsequent pathological remodeling (15). Various sources of oxidative stress have been implicated including mitochondria, xanthine oxidase and the non-phagocytic NADPH oxidases (16). There is evidence to suggest that administration of antioxidant agents inhibit pathological remodeling (17-21). There is also evidence to suggest that administration of various types of cells into injured myocardium, or systemically may inhibit pathological remodeling (22, 23). However, to date, there has been no concurrent inhibition of inflammatory responses together with cellular therapy. The importance of the combination is that inflammatory agents are often inhibitory to stem cell activity. For example, it is known that inflammatory agents such as TNF-alpha inhibit ability of stem cells to self renew (24, 25). Additionally, stem cells are known to be particularly sensitive to oxidative stress (26, 27). The particular sensitivity of stem cells to oxidative stress may explain their increased viability and function under conditions of hypoxia (28-32). Accordingly, in an embodiment of the invention, cells with potential to repair cardiovascular tissue is used in conjunction antioxidant administration in order to induce repair of cardiovascular disease.

In a specific embodiment, patients suffering a myocardial infarction are revascularized using procedures known in the art. Said procedures include administration of thrombolytics such as tissue plasminogen activator (TPA) and/or introduction of a single or plurality of stents in order to allow perfusion of the infarct related artery. Subsequent to revascularization, said patients are treated with cells capable of causing cardiac repair. Said cells may be, in one embodiment, mesenchymal stem cells. It is known in the art that mesenchymal stem cells induce both anti-inflammatory effects, as well as ability to provide trophic factors that accelerate muscle repair. In conjunction with mesenchymal stem cells, patients are treated with expanded CD34 cells. Without being bound to theory, the combination of mesenchymal stem cells and CD34 cells are used to concurrently induce angiogenesis, as well as provide healing and reparative growth factors. In conjunction with cell administration, patients are treated with antioxidants. In one embodiment intravenous ascorbic acid is administered concurrently with cell therapy. In specific embodiments it is necessary to provide intravenous ascorbic acid in order to attain a higher concentration of ascorbic acid in systemic circulation than can be achieved through other means of administration such as oral. It was recently published that only intravenous administration of ascorbic acid, but not oral, can attain certain levels of plasma ascorbic acid necessary to induce pharmacological concentrations of ascorbate in the plasma (33). In other studies it was demonstrated that intravenous administration of ascorbic acid was able to achieve a 140-fold higher dose than those from maximum oral doses (34). The need in some cases to use intravenous administration is due to the tight control of plasma ascorbic acid during oral administration. Depending on clinical outcome, additional cells and/or antioxidants may be provided. In one embodiment, mesenchymal stem cells are provided in absence of cord CD34 cells with the purpose that mesenchymal stem cells will inhibit inflammation and function with enhanced benefit in the presence of one or more antioxidants. In one embodiment, CD34 cells are provided in absence of mesenchymal stem cells with the purpose that CD34 cells will induce angiogenesis with enhanced benefit in the presence of one or more antioxidants. In some embodiments the therapy is performed in combination with a growth factor or a plurality of growth factors. This includes, without limitation, angiogenic factors and other molecules competent to induce angiogenesis, including acidic and basic fibroblast growth factors, vascular endothelial growth factor, hif-1, epidermal growth factor, transforming growth factor .alpha. and .beta., platelet-derived endothelial growth factor, platelet-derived growth factor, hepatocyte growth factor and insulin like growth factor; growth factors; BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Dependent on embodiment, cells, and/or growth factors, and/or antioxidants may be provided intravascularly, intravenously, intraarterially, intraperitoneally, via intraventricular infusion, via infusion catheter, via balloon catheter, via bolus injection, or via direct application to tissue.

In another embodiment, the invention provides the use of combined administration of stem cells with antioxidants for the treatment of ischemic heart disease. It is known that in ischemic heart disease an increased level of oxidative stress is present (35). Accordingly patients with ischemic heart disease are treated by combined use of cells such as combination of CD34 and mesenchymal stem cells as described above, along with the administration of one or more antioxidants. Various other cardiovascular conditions are amenable to treatment with the current invention; these include cardiomyopathy, post peripheral vascular disease, CNS vascular disease, congestive heart failure, ventricular septal defect, valvular defects, atrial septal defect, congenital heart defect, ventricular aneurysm, a condition requiring ventricular reconstruction, restenosis, cardiac hypertrophy, and heart failure.

EXAMPLE 1

50 patients with congestive heart failure (left ventricular ejection fraction <35%) are entered into a clinical trial. 25 are treated with placebo and stem cells, 25 receive stem cells and intravenous ascorbic acid (active treatment). Active treatment comprises of 25 grams of intravenous ascorbic acid given in 250 ml of saline intravenously. The ascorbic acid is allowed to drip for 30 to 40 minutes into the patient. 4 hours after, 5 million CD34 cells derived from cord blood are given intravenously and 3 million mesenchymal stem cells are given intravenously. Cells are given for 4 consecutive days. Followed up a 2 day rest period. On day 7 cells are administered again, 5 million CD34 and 3 million mesenchymal cells, along with the same concentration of ascorbic acid as given on day 1. After a period of 4 weeks an improvement is seen ejection fraction and clinical heart failure score in both groups as compared to pre-treatment. Improvement is significantly higher in the patients who have received ascorbic acid together with the stem cells.

Mesenchymal cells are prepared as described in as described in Meng et al. *Endometrial regenerative cells: a novel stem cell population. J Transl Med.* 2007 Nov. 15; 5:57). CD34 cells are extracted and expanded as described below.

Umbilical cord blood is purified according to routine methods ((Rubinstein, et al. *Processing and cryopreservation of placental/umbilical cord blood for unrelated bone marrow reconstitution. Proc Natl Acad Sci USA* 92:10119-10122). Briefly, a 16-gauge needle from a standard Baxter 450-ml blood donor set containing CPD A anticoagulant (citrate/phosphate/dextrose/adenine) (Baxter Health Care, Deerfield, Ill.) is inserted and used to puncture the umbilical vein of a placenta obtained from healthy delivery from a mother tested for viral and bacterial infections according to international donor standards. Cord blood is allowed to drain by gravity so as to drip into the blood bag. The placenta is placed in a plastic-lined, absorbent cotton pad suspended from a specially constructed support frame in order to allow collection and reduce the contamination with maternal blood and other secretions. The 63 ml of CPD A used in the standard blood transfusion bag, calculated for 450 ml of blood, is reduced to 23 ml by draining 40 ml into a graduated cylinder just prior to collection. This volume of anticoagulant matches better the cord volumes usually retrieved (<170 ml).

An aliquot of the blood is removed for safety testing according to the standards of the National Marrow Donor Program (NMDP) guidelines. Safety testing includes routine laboratory detection of human immunodeficiency virus 1 and 2, human T-cell lymphotrophic virus I and II, Hepatitis B virus, Hepatitis C virus, Cytomegalovirus and Syphilis. Subsequently, 6% (wt/vol) hydroxyethyl starch is added to the anticoagulated cord blood to a final concentration of 1.2%.

The leukocyte rich supernatant is then separated by centrifuging the cord blood hydroxyethyl starch mixture in the original collection blood bag (50×g for 5 min at 10° C.). The leukocyte-rich supernatant is expressed from the bag into a 150-ml Plasma Transfer bag (Baxter Health Care) and centrifuged (400×g for 10 min) to sediment the cells. Surplus supernatant plasma is transferred into a second plasma Transfer bag without severing the connecting tube. Finally, the sedimented leukocytes are resuspended in supernatant plasma to a total volume of 20 ml. Approximately $5 \times 10^8$-$7 \times 10^9$ nucleated cells are obtained per cord. Cells are cryopreserved according to the method described by Rubinstein et al (Rubinstein, et al. *Processing and cryopreservation of placental/umbilical cord blood for unrelated bone marrow reconstitution. Proc Natl Acad Sci USA* 92:10119-10122). for subsequent cellular therapy. CD34 cells are expanded by culture. CD34+ cells are purified from the mononuclear cell fraction by immuno-magnetic separation using the Magnetic Activated Cell Sorting (MACS) CD34+ Progenitor Cell Isolation Kit (Miltenyi-Biotec, Auburn, Calif.) according to manufacturer's recommendations. The purity of the CD34+ cells obtained ranges between 95% and 98%, based on Flow Cytometry evaluation (FACScan flow cytometer, Becton-Dickinson, Immunofluorometry systems, Mountain View, Calif.). Cells are plated at a concentration of $10.\sup.4$ cells/ml in a final volume of 0.5 ml in 24 well culture plates (Falcon; Becton Dickinson Biosciences) in DMEM supplemented with the cytokine cocktail of: 20 ng/ml IL-3, 250 ng/ml IL-6, 10 ng/ml SCF, 250 ng/ml TPO and 100 ng/ml flt-3L and a 50% mixture of LPCM. LPCM is generated by obtaining a fresh human placenta from vaginal delivery and placing it in a sterile plastic container. The placenta is rinsed with an anticoagulant solution comprising phosphate buffered saline (Gibco-Invitrogen, Grand Island, N.Y.), containing a 1:1000 concentration of heparin (1% w/w) (American Pharmaceutical Partners, Schaumburg, Ill.). The placenta is then covered with a DMEM media (Gibco) in a sterile container such that the entirety of the placenta is submerged in said media, and incubated at 37.degree. C. in a humidified 5% $CO_2$ incubator for 24 hours. At the end of the 24 hours, the live placenta conditioned medium (LPCM) is isolated from the container and sterile-filtered using a commercially available sterile 0.2 micron filter (VWR). Cells are expanded, checked for purity using CD34-specific flow cytometry and immunologically matched to recipients using a mixed lymphocyte reaction. Cells eliciting a low level of allostimulatory activity to recipient lymphocytes are selected for transplantation. Cells are administered as described above.

EXAMPLE 2

Patient 242 was diagnosed with dilated, non-ischemic cardiomyopathy in 2002 with an ejection fraction of approximately 30% as measured by echocardiogram (ECHO). The clinical presentation at diagnosis was indicative of congestive heart failure, including marked dyspnea, inability to exercise, dizziness, and irregular heart beat. New York Heart Association (NYHA) classification of II. ECHO analysis in April 2003 indicated ejection fraction of approximately 40%. Quality of life assessment using the Minnesota Living with Heart Failure Questionnaire (Middel, Bouma et al. 2001) revealed a score of 90. The patient was treated under informed consent in December 2006 with a combination of cord blood expanded allogeneic CD34 cells (2.5 million) and placentally derived allogeneic mesenchymal stem cells (3 million) 3 times over the period of a week. Ascorbic acid was administered intravenously during this period at a concentration of 25 grams intravenously given in 250 ml of saline over a 30 to 40 minute period on day 1 and 7 of treatment.

Cellular therapy was well tolerated and no adverse side effects were observed either acutely or as of this writing. The patient did not experience either symptoms of either acute (skin rash of diarrhea) or chronic (skin rash, skin inflammation, mouth lesions, hair loss, indigestion) graft vs. host disease. Two weeks prior to an echocardiogram in April 2007, the patient voluntarily discontinued all above-mentioned medications and supplements. The echocardiogram revealed an ejection fraction of 50-55%. The patient reports profound clinical benefit at time of writing (April, 2008), including resolution of heart-failure associated symptoms of dizziness, fatigue, dyspnea, rapid heart beat, irregular heart beat, depression, blackouts, and loss of sleep secondary to orthopnea. The Minnesota Living with Heart Failure Questionnaire score was zero. The patient has a normal ejection fraction and no symptoms of heart failure and is no longer classifiable on the NYHA scale.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

REFERENCES

1. Klein, H. M., Ghodsizad, A., Marktanner, R., Poll, L., Voelkel, T., Mohammad Hasani, M. R., Piechaczek, C., Feifel, N., Stockschlaeder, M., Burchardt, E. R., et al. 2007. Intramyocardial implantation of CD133+ stem cells improved cardiac function without bypass surgery. *Heart Surg Forum* 10:E66-69.
2. Patel, A. N., Geffner, L., Vina, R. F., Saslavsky, J., Urschel, H. C., Jr., Kormos, R., and Benetti, F. 2005. Surgical treatment for congestive heart failure with autologous adult stem cell transplantation: a prospective randomized study. *J Thorac Cardiovasc Surg* 130:1631-1638.
3. Schachinger, V., Erbs, S., Elsasser, A., Haberbosch, W., Hambrecht, R., Holschermann, H., Yu, J., Corti, R., Mathey, D. G., Hamm, C. W., et al. 2006. Intracoronary bone marrow-derived progenitor cells in acute myocardial infarction. *N Engl J Med* 355:1210-1221.
4. Tendera, M., and Wojakowski, W. 2005. Clinical trials using autologous bone marrow and peripheral blood-derived progenitor cells in patients with acute myocardial infarction. *Folia Histochem Cytobiol* 43:233-235.
5. Dawn, B., Zuba-Surma, E. K., Abdel-Latif, A., Tiwari, S., and Bolli, R. 2005. Cardiac stem cell therapy for myocardial regeneration. A clinical perspective. *Minerva Cardioangiol* 53:549-564.
6. Zhang, S., Wang, D., Estrov, Z., Raj, S., Willerson, J. T., and Yeh, E. T. 2004. Both cell fusion and transdifferentiation account for the transformation of human peripheral blood CD34-positive cells into cardiomyocytes in vivo. *Circulation* 110:3803-3807.
7. Ye, L., Haider, H., and Sim, E. K. 2006. Adult stem cells for cardiac repair: a choice between skeletal myoblasts and bone marrow stem cells. *Exp Biol Med (Maywood)* 231:8-19.
8. de Nigris, F., Williams-Ignarro, S., Sica, V., D'Armiento, F. P., Lerman, L. O., Byrns, R. E., Sica, G., Fiorito, C., Ignarro, L. J., and Napoli, C. 2007. Therapeutic effects of concurrent autologous bone marrow cell infusion and metabolic intervention in ischemia-induced angiogenesis in the hypercholesterolemic mouse hindlimb. *Int J Cardiol* 117:238-243.
9. Gotto, A. M., Jr. 2007. Role of C-reactive protein in coronary risk reduction: focus on primary prevention. *Am J Cardiol* 99:718-725.
10. Sanchez, P. L., and Mazzone, A. M. 2006. C-reactive protein in aortic valve disease. *Cardiovasc Ultrasound* 4:37.
11. Genest, J. 2004. Preventive cardiology: Move over low density lipoprotein cholesterol, hello C-reactive protein? *Can J Cardiol* 20 Suppl B:89B-92B.
12. Langlois, M., Duprez, D., Delanghe, J., De Buyzere, M., and Clement, D. L. 2001. Serum vitamin C concentration is low in peripheral arterial disease and is associated with inflammation and severity of atherosclerosis. *Circulation* 103:1863-1868.
13. Ullegaddi, R., Powers, H. J., and Gariballa, S. E. 2005. Antioxidant supplementation enhances antioxidant capacity and mitigates oxidative damage following acute ischaemic stroke. *Eur J Clin Nutr* 59:1367-1373.
14. Block, G., Jensen, C., Dietrich, M., Norkus, E. P., Hudes, M., and Packer, L. 2004. Plasma C-reactive protein concentrations in active and passive smokers: influence of antioxidant supplementation. *J Am Coll Nutr* 23:141-147.
15. Neuzil, J., Rayner, B. S., Lowe, H. C., and Witting, P. K. 2005. Oxidative stress in myocardial ischaemia reperfusion injury: a renewed focus on a long-standing area of heart research. *Redox Rep* 10:187-197.
16. Grieve, D. J., Byrne, J. A., Cave, A. C., and Shah, A. M. 2004. Role of oxidative stress in cardiac remodelling after myocardial infarction. *Heart Lung Circ* 13:132-138.

17. Mellin, V., Isabelle, M., Oudot, A., Vergely-Vandriesse, C., Monteil, C., Di Meglio, B., Henry, J. P., Dautreaux, B., Rochette, L., Thuillez, C., et al. 2005. Transient reduction in myocardial free oxygen radical levels is involved in the improved cardiac function and structure after long-term allopurinol treatment initiated in established chronic heart failure. *Eur Heart J* 26:1544-1550.

18. Qin, F., Yan, C., Patel, R., Liu, W., and Dong, E. 2006. Vitamins C and E attenuate apoptosis, beta-adrenergic receptor desensitization, and sarcoplasmic reticular Ca2+ ATPase downregulation after myocardial infarction. *Free Radic Biol Med* 40:1827-1842.

19. Onogi, H., Minatoguchi, S., Chen, X. H., Bao, N., Kobayashi, H., Misao, Y., Yasuda, S., Yamaki, T., Maruyama, R., Uno, Y., et al. 2006. Edaravone reduces myocardial infarct size and improves cardiac function and remodelling in rabbits. *Clin Exp Pharmacol Physiol* 33:1035-1041.

20. Gasparetto, C., Malinvemo, A., Culacciati, D., Gritti, D., Prosperini, P. G., Specchia, G., and Ricevuti, G. 2005. Antioxidant vitamins reduce oxidative stress and ventricular remodeling in patients with acute myocardial infarction. *Int J Immunopathol Pharmacol* 18:487-496.

21. Sia, Y. T., Lapointe, N., Parker, T. G., Tsoporis, J. N., Deschepper, C. F., Calderone, A., Pourdjabbar, A., Jasmin, J. F., Sarrazin, J. F., Liu, P., et al. 2002. Beneficial effects of long-term use of the antioxidant probucol in heart failure in the rat. *Circulation* 105:2549-2555.

22. Singla, D. K., Lyons, G. E., and Kamp, T. J. 2007. Transplanted Embryonic Stem Cells Following Mouse Myocardial Infarction Inhibit Apoptosis and Cardiac Remodeling. *Am J Physiol Heart Circ Physiol*.

23. Kang, H. J., Kim, H. S., Koo, B. K., Kim, Y. J., Lee, D., Sohn, D. W., Oh, B. H., and Park, Y. B. 2007. Intracoronary infusion of the mobilized peripheral blood stem cell by G-CSF is better than mobilization alone by G-CSF for improvement of cardiac function and remodeling: 2-year follow-up results of the Myocardial Regeneration and Angiogenesis in Myocardial Infarction with G-CSF and Intra-Coronary Stem Cell Infusion (MAGIC Cell) 1 trial. *Am Heart J* 153:237 e231-238.

24. Dybedal, I., Bryder, D., Fossum, A., Rusten, L. S., and Jacobsen, S. E. 2001. Tumor necrosis factor (TNF)-mediated activation of the p55 TNF receptor negatively regulates maintenance of cycling reconstituting human hematopoietic stem cells. *Blood* 98:1782-1791.

25. Bryder, D., Ramsfjell, V., Dybedal, I., Theilgaard-Monch, K., Hogerkorp, C. M., Adolfsson, J., Borge, O. J., and Jacobsen, S. E. 2001. Self-renewal of multipotent long-term repopulating hematopoietic stem cells is negatively regulated by Fas and tumor necrosis factor receptor activation. *J Exp Med* 194:941-952.

26. Ito, K., Hirao, A., Arai, F., Takubo, K., Matsuoka, S., Miyamoto, K., Ohmura, M., Naka, K., Hosokawa, K., Ikeda, Y., et al. 2006. Reactive oxygen species act through p38 MAPK to limit the lifespan of hematopoietic stem cells. *Nat Med* 12:446-451.

27. Ito, K., Hirao, A., Arai, F., Matsuoka, S., Takubo, K., Hamaguchi, I., Nomiyama, K., Hosokawa, K., Sakurada, K., Nakagata, N., et al. 2004. Regulation of oxidative stress by ATM is required for self-renewal of haematopoietic stem cells. *Nature* 431:997-1002.

28. Wang, F., Thirumangalathu, S., and Loeken, M. R. 2006. Establishment of new mouse embryonic stem cell lines is improved by physiological glucose and oxygen. *Cloning Stem Cells* 8:108-116.

29. Ingram, D. A., Krier, T. R., Mead, L. E., McGuire, C., Prater, D. N., Bhavsar, J., Saadatzadeh, M. R., Bijangi-Vishehsaraei, K., Li, F., Yoder, M. C., et al. 2007. Clonogenic endothelial progenitor cells are sensitive to oxidative stress. *Stem Cells* 25:297-304.

30. Moussavi-Harami, F., Duwayri, Y., Martin, J. A., and Buckwalter, J. A. 2004. Oxygen effects on senescence in chondrocytes and mesenchymal stem cells: consequences for tissue engineering. *Iowa Orthop J* 24:15-20.

31. D'Ippolito, G., Diabira, S., Howard, G. A., Roos, B. A., and Schiller, P. C. 2006. Low oxygen tension inhibits osteogenic differentiation and enhances stemness of human MIAMI cells. *Bone* 39:513-522.

32. Lennon, D. P., Edmison, J. M., and Caplan, A. I. 2001. Cultivation of rat marrow-derived mesenchymal stem cells in reduced oxygen tension: effects on in vitro and in vivo osteochondrogenesis. *J Cell Physiol* 187:345-355.

33. Chen, Q., Espey, M. G., Krishna, M. C., Mitchell, J. B., Corpe, C. P., Buettner, G. R., Shacter, E., and Levine, M. 2005. Pharmacologic ascorbic acid concentrations selectively kill cancer cells: action as a pro-drug to deliver hydrogen peroxide to tissues. *Proc Natl Acad Sci USA* 102:13604-13609.

34. Padayatty, S. J., Sun, H., Wang, Y., Riordan, H. D., Hewitt, S. M., Katz, A., Wesley, R. A., and Levine, M. 2004. Vitamin C pharmacokinetics: implications for oral and intravenous use. *Ann Intern Med* 140:533-537.

35. Bevan, R. J., Durand, M. F., Hickenbotham, P. T., Kitas, G. D., Patel, P. R., Podmore, I. D., Griffiths, H. R., Waller, H. L., and Lunec, J. 2003. Validation of a novel ELISA for measurement of MDA-LDL in human plasma. *Free Radic Biol Med* 35:517-527.

What is claimed is:

1. A method of ameliorating the effects of congestive heart failure comprising: a) identifying a subject suffering from congestive heart failure b) harvesting $CD34^+$ cells from umbilical cord blood mononuclear stem cells; c) intravenously injecting said $CD34^+$ cells into said subject; d) intravenously administering mesenchymal stem cells to said subject and e) administering ascorbic acid or a derivative thereof intravenously to said subject to ameliorate the effects of congestive heart failure.

2. The method of claim 1, wherein said ascorbic acid is administered intravenously in an amount of 15-700 g/week.

3. The method of claim 1, wherein said ascorbic acid is administered intravenously in an amount of 25 g/day.

4. The method of claim 1, wherein said ascorbic acid is intravenously administered to said subject prior to the administration of said $CD34^+$ cells and mesenchymal stem cells.

5. The method of claim 1, further comprising measuring oxidative stress in said subject prior to administration of said $CD34^+$ cells and mesenchymal stem cells, and wherein the ascorbic acid is intravenously administrated at a concentration and frequency based upon said measurement of oxidative stress.

6. The method of claim 1, wherein the subject is tested after being administered the ascorbic acid, $CD34^+$ cells, and mesenchymal stem cells and there is an improvement in ejection fraction and clinical heart failure score.

7. The method of claim 1, wherein the subject is tested after being administered the ascorbic acid, $CD34^+$ cells, and mesenchymal stem cells and there is an improvement in ejection fraction.

8. The method of claim 1, wherein the subject is tested after being administered the ascorbic acid, $CD34^+$ cells, and mesenchymal stem cells and there is an improvement in clinical heart failure score.

* * * * *